United States Patent
Gu

(10) Patent No.: US 7,534,600 B2
(45) Date of Patent: May 19, 2009

(54) RAPID BACTERIAL QUANTIFICATION

(75) Inventor: Haoyi Gu, Yarmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 11/434,287

(22) Filed: May 15, 2006

(65) Prior Publication Data

US 2006/0263845 A1 Nov. 23, 2006

Related U.S. Application Data

(63) Continuation of application No. PCT/US06/019299, filed on May 15, 2006, now abandoned.

(60) Provisional application No. 60/681,824, filed on May 17, 2005.

(51) Int. Cl.
*C12M 1/34* (2006.01)
*C12M 1/12* (2006.01)

(52) U.S. Cl. .............. 435/288.4; 435/287.9; 435/297.2; 435/297.5; 435/308.1

(58) Field of Classification Search .............. 435/288.4, 435/297.2, 297.4
See application file for complete search history.

(56) References Cited

U.S. PATENT DOCUMENTS

| | | | | |
|---|---|---|---|---|
| 2,761,813 A | * | 9/1956 | Goetz | 435/297.5 |
| 2,923,669 A | * | 2/1960 | Poitras | 435/34 |
| 3,843,452 A | | 10/1974 | Freake et al. | |
| 3,929,583 A | | 12/1975 | Sharpe et al. | |
| 4,317,726 A | * | 3/1982 | Shepel | 210/236 |
| 4,485,171 A | | 11/1984 | Ikeda et al. | |
| 4,493,815 A | | 1/1985 | Fernwood et al. | |
| 5,039,493 A | * | 8/1991 | Oprandy | 422/101 |
| 5,288,638 A | * | 2/1994 | Lemonnier | 422/101 |
| 5,380,437 A | * | 1/1995 | Bertoncini | 210/416.1 |
| 5,905,038 A | * | 5/1999 | Parton | 435/287.6 |
| 2003/0082516 A1 | | 5/2003 | Straus | |
| 2004/0219628 A1 | | 11/2004 | Yoshikazu et al. | |

FOREIGN PATENT DOCUMENTS

NL 1007489 A * 10/2000

OTHER PUBLICATIONS

International Search Report for corresponding PCT application No. PCT/US2006/019299 dated Oct. 13, 2006.
U.S. Appl. No. 60/681,824, filed May 17, 2005.

* cited by examiner

*Primary Examiner*—William H Beisner
(74) *Attorney, Agent, or Firm*—McDonnell Boehnen Hulbert & Berghoff LLP

(57) ABSTRACT

The invention provides devices and methods for rapid quantification of microorganisms and cells. In one embodiment, the devices comprise a container having an upper compartment and a lower compartment, wherein the upper compartment is connected to a passage through which a fluid sample can flow and enter the upper compartment, and wherein the lower compartment is connected to a passage through which a fluid sample can flow and exit the lower compartment; a mounting structure upon which a filter can be positioned; a filter, wherein the filter separates the upper compartment from the lower compartment, wherein the filter comprises a chromogen; a first template covering the filter, wherein the first template comprises a predetermined number of holes through which a liquid sample can flow through to discrete locations on the filter; and an absorbent pad under the filter and in contact with the filter.

12 Claims, 4 Drawing Sheets

Sample Processing Field Unit

12v/Mains power

RAPID BACTERIAL QUANTIFICATION

PRIORITY

This application claims the benefit of U.S. Appl. Ser. No. 60/681,824, filed May 17, 2005, which is incorporated herein by reference in its entirety. This application also is a continuation of PCT/US06/019299, filed May 15, 2006, now abandoned.

FIELD OF THE INVENTION

The invention relates to methods and devices for detecting and quantifying microorganisms and cells in a sample.

BACKGROUND OF THE INVENTION

Many industries need to detect and quantify the concentration and level of biological material in a sample. For example, the determination of bacterial concentration in food and water is an essential part of food and water quality testing. EPA regulations require that no coliforms, such as *Escherichia coli*, be present in potable water. The "presence/absence" format of a testing medium, such as Colilert® chemical mixture (IDEXX Laboratories, Me.), which is used as a testing medium for *Escherichia coli* and all coliform bacteria, is very useful in making this determination.

However, there are areas where the quantification, not just the detection, of microorganism concentration is important. Examples of such areas include waste water, incoming water in water purification systems, surface water, and food testing.

SUMMARY OF THE INVENTION

One embodiment of the invention provides a detection device comprising an absorbent pad, wherein the absorbent pad comprises a growth medium or a detection medium or a combination thereof, a filtration membrane on top of and in contact with the absorbent pad, and a liquid impermeable template on top of and in contact with the filtration membrane, wherein the template comprises a predetermined number of holes through which a liquid sample can flow. The detection device can comprise two substantially identical templates, wherein the filtration membrane is between the two templates.

Another embodiment of the invention provides a detection device comprising a container having an upper compartment and a lower compartment, wherein the upper compartment is connected to a passage through which a fluid sample can flow and enter the upper compartment. The lower compartment is connected to a passage through which a fluid sample can flow and exit the lower compartment. The device also comprises a mounting structure upon which a filter can be positioned, wherein the filter separates the upper compartment from the lower compartment and a template covering the filter. The template comprises a predetermined number of holes through which a liquid sample can flow through to discrete locations on the filter. The upper compartment can be separable from the lower compartment by, for example, twisting the upper compartment relative to the lower compartment. The filter can be between two substantially similar templates. The discrete locations on the filter can have an area of about 100 square millimeters or less. The template can comprise at least about 10, 20, 50, or 100 holes. The template can be sealed or compressed onto the filter. The template can be plastic. The filter can comprise a chromogen, such as an enzyme substrate that can be hydrolyzed by enzymes produced by a microorganism or cell. The filter can comprise one or more different enzyme substrates at one or more different discrete locations.

Still another embodiment of the invention can provide a method for determining the presence or absence of one or more target microorganisms or target cells in a fluid sample. The method can comprise applying a fluid sample potentially comprising target microorganisms or target cells through a filter of a detection device of the invention, wherein microorganisms or cells present in the fluid sample are captured onto the filter. The filter is incubated in a medium and the presence or absence of microorganisms on the filter are determined. The medium can be a differential medium that supports growth of microorganisms or cells and allows for detection and quantification or both detection and quantification of target microorganisms or cells within about 4 to about 6 hours. The device or sample can comprise one or more chromogens, wherein the chromogens are one or more enzyme substrates, fluorescent compounds, chemiluminescent compounds, radioactive elements, direct visual labels, cofactors, inhibitors, or magnetic particles. The detecting can comprise exposing the filter to ultraviolet light at a wavelength or wavelengths capable of exciting one or more hydrolyzed enzyme substrates. The one or more enzyme substrates can be fluorescein di-$\beta$-D-galactopyranoside, 4-methylumbelliferyl-$\beta$-D-glucuronide, 6-chloro-4-trifluoromethylumbelliferyl-beta-D-galactopyranoside, or 6-chloro-4-methylumbelliferyl-beta-D-glucuronide. The method can further comprise quantifying the number of target cells or target microorganisms, using, for example, the most probable number technique.

DETAILED DESCRIPTION OF THE INVENTION

Devices

Figure 1:
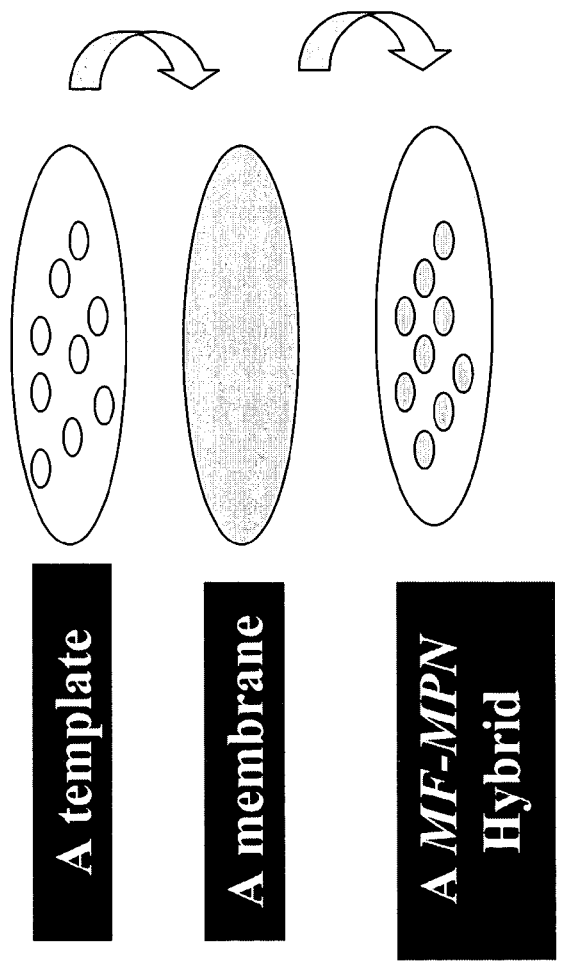
FIG. 1 shows a schematic representation of a device of the invention.

A device of the invention comprises a filter having a plurality of discrete, pre-determined locations where microorganisms or cells can be captured. In one embodiment, the discrete locations can be created on the filter using a template. See e.g., FIG. 1. A template can comprise a plurality of holes and can be sealed onto a filter or compressed onto a filter, thereby providing discrete locations on the filter. The template is preferably non-permeable to liquid, which prevents a liquid sample from bleeding onto multiple locations on a filter. In one embodiment, a filter can be sandwiched between two substantially identical templates. The template or templates and the filter can be in contact with each other.

Figure 4:
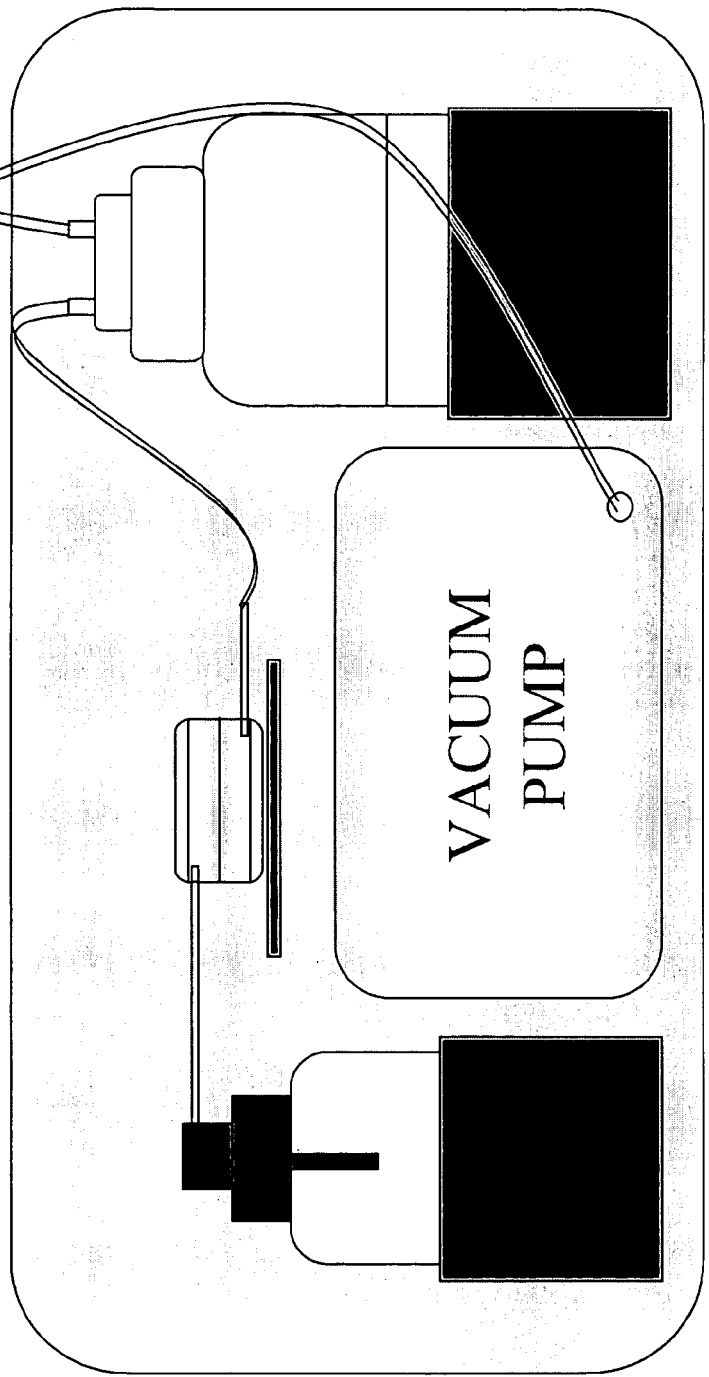
FIG. 4 shows an example of a sample field processing unit.

In one embodiment of the invention, a device of the invention comprises two compartments, an upper compartment and a lower compartment, which are separated by a filter. See e.g., FIG. 4. Each compartment can be attached to a passage as shown in FIG. 4. The passage attached to the upper compartment allows a fluid sample to flow into the upper compartment. The passage attached to the lower compartment allows a fluid sample, which flows from the upper compartment, to exit the lower compartment.

The upper and lower compartment can be separably attached and a filter can be positioned on a mounting structure, so that when the compartments are separated the filter can be removed. The filter can have a plurality of discrete, pre-determined locations where microorganisms or cells can be captured. A template can be present on top of a filter or a filter can be sandwiched between two substantially identical templates. The template or templates and the filter can be in contact with each other. The compartments can be separably attached using any means known in the art. For example, the upper compartment can be made to separate from the lower compartment by, e.g., twisting the two compartments in opposite directions. Alternatively, the compartments can be made to snap-fit together. Preferably, the two compartments are attached so that no liquid can leak around the attached area, for example, by providing a seal or gasket to prevent liquid from seeping at the points of attachment.

In certain embodiments, a liquid sample to be filtered can be placed in an upper compartment above the filter and can be drawn through the filter by any suitable means, such as a vacuum pump or syringe. The filtered liquid can be withdrawn through the passage in the lower compartment. Microorganisms or cells in a liquid sample will be captured by the filter at the discrete locations.

Once microorganisms, such as bacteria, are captured by a filter, they can be grown in a suitable medium. For example, the filter can be removed from the device and placed into an appropriate container comprising media, such as selective media as described herein. Alternatively, a device of the invention can comprise an absorbent pad in contact with the filter, which can be used to provide media to microorganisms or cells on the filter. Where an absorbent pad is used, media can be placed into the lower compartment after the liquid sample has been removed so that the media is in contact with the absorbent pad and the absorbent pad is in contact with the filter. Alternatively, a filter with or without a template and absorbent pad can be placed into or on a liquid or semi-solid media. The absorbent pad can serve as a wick, drawing media from the lower compartment and allowing the microorganisms attached to the filter to use the media for growth. Alternatively, an absorbent pad can comprise dried media that is rehydrated when contacted with a liquid sample. In another embodiment the device does not comprise an absorbent pad. A filter used to capture microorganisms or cells from a sample, with or without the template, is contacted directly with a liquid or semi-solid medium or is used without any contact with a medium.

Therefore, the devices of the invention can act as a membrane filtration (MF)/most probable number (MPN) hybrid device by concentrating microorganisms or cells and providing quantification information. The advantages of using a MF/MPN device of the invention include sample concentration, reaction site registration (pre-determined knowledge of the location of reaction sites) localized presence/absence determination, and quantification via, e.g., most probable numbers (MPN).

Microorganisms that can be detected and/or quantified using a device and/or methods of the invention can be, for example, bacteria, protozoa, algae, and fungi. Additionally, any cells that can be retained by a filter can be detected and/or quantified.

Template

A template of the invention can be made of any material that is non-permeable to a liquid, for example a non-permeable film. For example, non-permeable materials include polyurethane, plastic, PVC, polyethylene, polycarbonates, metal, glass.

A template of the invention can comprise any number of holes. In certain embodiments, a template comprises a pre-determined number of holes, for example, at least about 10, 20, 30, 40, 50, 60, 70, 80, 90, 100 or more holes. The holes can be any shape and arranged in any pattern. In other embodiments, each hole creates an area on a filter of about 1, 5, 10, 50, 100, 1,000 square millimeters or less.

Filter

A filter used in a device of the invention can be any filter that permits a liquid sample to flow through and does not allow the target organism or cell to flow through the filter. For example, a filter can be a fiber glass filter or a membrane, such as a nitrocellulose membrane, a nylon membrane. A template as described above is in contact with or is part of a filter of the invention. The predetermined holes of the template allow a sample to flow through the filter only at the predetermined holes producing discrete locations on the filter. That is, the regions where a sample is allowed to flow through the template and then the filter define the discrete locations on the filter. Any microorganisms or cells present in the sample will be captured onto the filter at the discrete locations.

In other embodiments, a filter can have specific substrates attached at the discrete locations that can be used to detect microorganisms that produce a particular enzyme that is specific for the substrate. In such cases, microorganisms can cause a detectable change, such as a color change, that can be detected visually, for example by light microscopy or by eye.

In one embodiment of the invention, a filter is sealed or compressed onto the template of the invention. In another embodiment, a filter is sandwiched between two substantially identical templates, whose holes are lined up with each other. Substantially identical templates comprise the same number of predetermined holes. The filter can be sealed or compressed between the two templates.

Absorbent Pad

A suitable absorbent pad useful in a device of the invention includes, but is not limited to, cellulose, including for example, cellulose acetate; polymer foam, including for example, polymer foams comprising polyethers, polyesters, polypropylene, polyvinylchloride and polyurethanes. Typically, an absorbent pad suitable for a device of the invention has about 20 to 80 pores per centimeter.

Media

One of skill in the art will recognize that media, which is used in a device of the invention or used to grow or detect microorganisms or cells collected on a filter using a device of the invention, will vary depending on the type of microorganisms or cells that are believed present in a sample. A growth medium is a medium that can support growth of cells or microorganisms. A growth medium can also be a medium that merely sustains cells or microorganisms. A detection medium is a medium that allows for the detection of live cells or live microorganisms, dead cells or dead microorganisms, or both live and dead microorganisms and dead cells. A selective medium has a component or components that will inhibit or prevent the growth of certain types or species of microorganisms or cells and/or promote the growth of desired microorganisms or cells. The physical conditions of a culture medium, such as pH and temperature, can also be adjusted to render the medium selective for organisms that are able to grow under the conditions. A medium can also be a differential medium. A differential medium is a type of detection medium that enables the differentiation between different types of microorganisms, such as bacteria, or cells based on some observable trait in their pattern of growth on the medium.

In one embodiment of the invention media can be SG or SGII medium (COLILERT® or COLILERT-18® (IDEXX Laboratories, Westbrook, Me.) based media with additional carbon sources, such as glucose, sorbitol, lactose, ranging from 0.05 to 5.0 gram per liter). These media are selective for coliforms and *E. coli*, and are optimized for beta-galactosidase and beta-glucuronidase activities of the target bacteria. These media enable rapid detection of target organisms, e.g., coliforms, in about 4 to 6 hours in combination with an optical system.

In certain embodiments, the media comprises chromogens, such as enzyme substrates that can be hydrolyzed by a particular target microorganism or cell to produce a detectable color change (i.e., a differential medium). As used herein, a "chromogen" is any substance that provides a detectable change under appropriate conditions. For example, a chromogen can be a fluorophore that can be detected in ultraviolet (UV) light having certain wavelength. Other chromogens include catalysts such as enzyme substrates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular chromogen is not critical, but it will be capable of producing a signal either by itself or in conjunction with one or more additional substances.

Different enzyme substrates can be used to differentiate between multiple microorganisms in one liquid sample. For example, fluorescein di-β-D-galactopyranoside (FDG) can be hydrolyzed by coliforms and *E. coli*, while 4-methylumbelliferyl-β-δ-glucuronide (MUG) can be hydrolyzed by *E. Coli* but not by coliforms. When excited at 365 nm UV light, FDG has an emission peak at 525 nm and MUG has an emission peak at 450 nm. Thus, *E. coli* can be distinguished from coliforms in a sample by first detecting areas on a filter that generate a signal in UV light with a long-pass filter (such as λc=430 nm), and then determining which areas have *E. coli* using UV light and a band-pass filter (such as CWL 450 nm).

Other substrates can be used such as 6-chloro-4-trifluoromethylumbelliferyl-beta-D-galactopyranoside, which, when excited at 390-410 nm has an emission peak at 500 nm. 6-chloro-4-methylumbelliferyl-beta-D-glucuronide can also be used. When excited at 365-380 nm has an emission peak at 445 nm.

A chromogen can be attached to an absorbent layer, attached at discrete locations on a filter, present in media, added to a liquid sample, or added to a sample after microorganisms or cells are captured on a filter.

Visualization

Bacteria can grow to a detectable colony size in about 4 to about 6 hours on a filter area of about 0.45 μm. Microorganisms or cells attached to a filter at discrete locations can be detected using a camera, such as a CCD video camera as described herein. The images captured by camera can be analyzed using computer software as described in the Example below. Any methods known in the art can be used to detect cells and/or microorganisms on a filter of the invention.

Quantification

Figure 3:
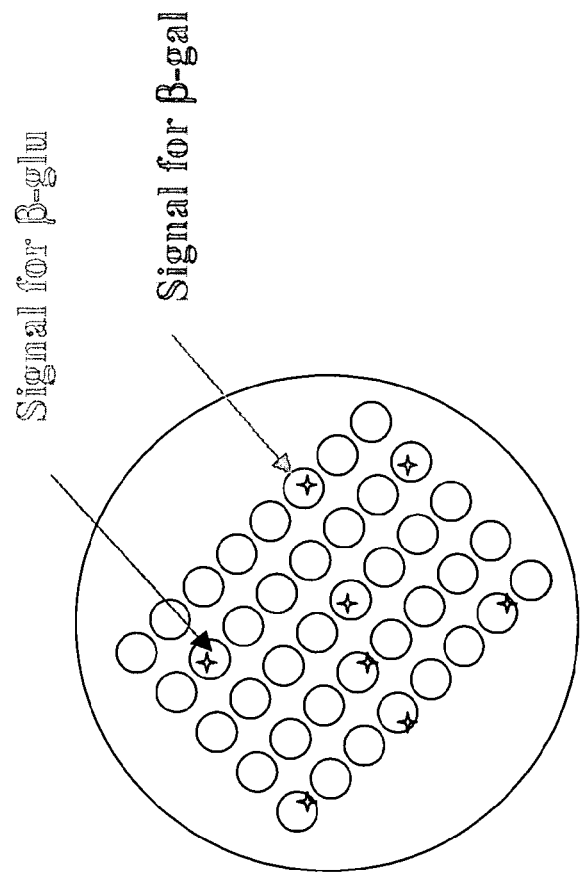
FIG. 3 shows a detection and quantification concept of the invention.

In certain embodiments, methods can be used to quantify the number of microorganisms or cells in a particular sample, e.g., the most probable number (MPN) method. (see, for example, Oblinger and Koburger, 1975, *J Milk Food Technol.* 38:540-545; Garthright and Blodgett, 2003, *Food Microbiology* 20:439-445). An illustration of how a device of the invention coupled with an image acquisition device, for example, a camera, can achieve a quantitative detection of coliforns and *E. coli* as shown in FIG. 3. The device has 40 sites. In this example, the camera detects signals from *E. coli* at 3 sites and signals from coliforms at 5 sites. The following formulation can be used to analyze the MPN:

MPN=(N)ln[N/(N–X)] (where N is the total number of sites, X is the number of sites with positive detection signal).

Therefore, the device of FIG. 3 has 40 discrete locations and 3 sites have *E. coli* as detected using the methods of the invention, and the total liquid sample volume was 100 ml, the MPN would be 4 cfu/100 ml *E. coli* and 5.6 cfu/100 ml coliforms.

Methods

Devices of the invention can be used to, for example, determine the presence or absence of one or more target microorganisms or target cells in a fluid sample. The fluid sample is applied to a filter of a detection device and microorganisms or cells present in the fluid sample are captured onto the filter. The filter can be incubated on a medium or can be immediately used to detect the presence or absence of cells or microorganisms. If a medium is used, the medium can be a differential medium that supports growth of microorganisms or cells and allows for detection and quantification or both detection and quantification of target microorganisms or cells within about, for example 4 to about 6 hours.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLE

Figure 2:
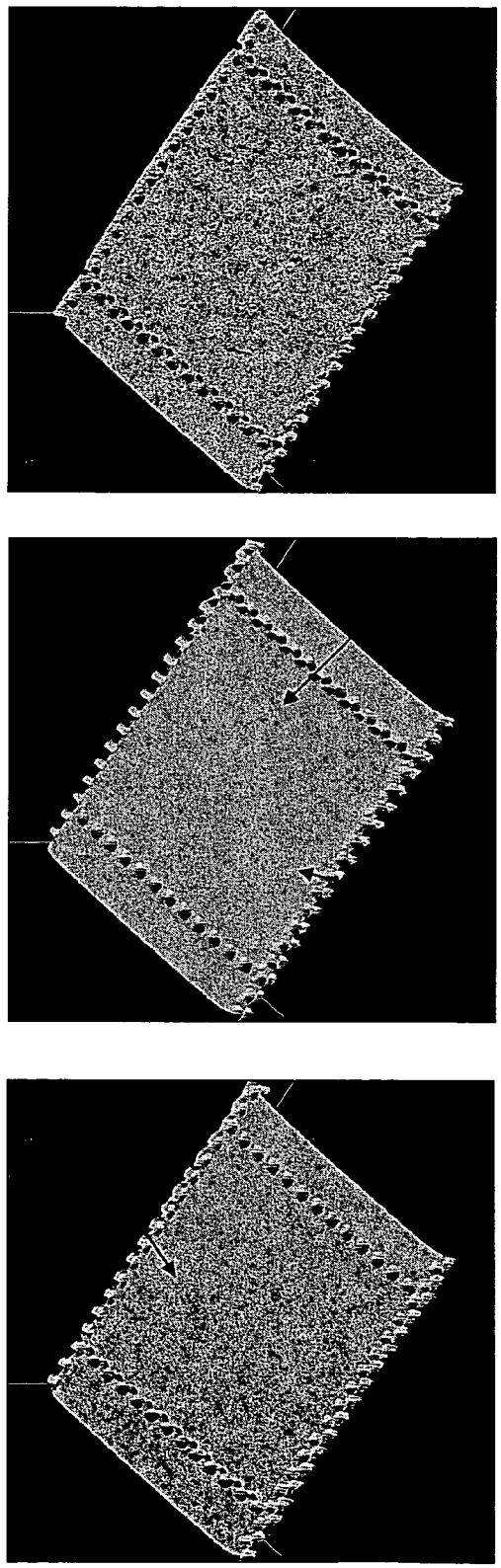
FIG. 2 shows growth of *E. coli, C. freundii*, and *Kl. pneumoniae* after 5 hours of incubation time in growth media.

Bacterial strains of *E. coli* (ATCC 25922), *C. freundii* (ATCC 8090), and *Kl. pneumoniae* (ATCC 31488) from a serial dilution were inoculated onto a 3 mm by 3 mm area of a 0.45 μm nitrocellulose membrane to mimic a single site of a device of the 5 invention. The membrane was placed onto an absorbent pad containing liquid media (re-optimized COLI-LERT®-18 (SGII medium)). (IDEXX Laboratories, Inc., Westbrook, Me.). Samples were incubated for 4-5 hours at 35° C. Colony growth was observed using a DXC-9000 3CCD video camera with a VZM 450i zoom lens (Sony Corp., New York, N.Y.), Flashpoint™ 128 Frame Grabber (TransTech Systems Ltd, United Kingdom), a fiber optic ring light, and Image-Pro® Plus 4.1 software (MediaCybernetics Corp., San Diego, Calif.). The results are shown in FIG. 2, demonstrating that target bacteria can be detected after 5 hours of incubation time on discrete areas of a membrane filter.

To verify the detection of bacterial growth at 5 hours was indeed bacteria, the samples were allowed to incubate for an additional 19 hours (for a total of 24 hours). The colonies detected at 5 hours were indeed bacterial growth.

The methodology described above was used to compare the device of the invention to a Colilert®/Qtray detection device. The results are shown in Table 1.

TABLE 1

| Strains | MPN/MF Concept using Imaging (~5 h. incubation at 35° C.) | Colilert ®/Qtray (CFU) (24 hour incubation at 35° C.) |
|---|---|---|
| E. coli (Norwalk Raw water) | 4 | 3 |
| E. coli (ATCC 25922) | 4 | 5.3 |
| E. coli (SCCRWA 5144572) | 20 | 16.4 |
| C. freundii (ATCC 8090) | 12 | 13.7 |
| C. freundii (Burlington) | 4 | 3 |
| Ent. cloacae (ATCC 18047) | 5 | 4 |
| Ent. aerogenes (EPA 11703) | 18 | 20.7 |
| Kl. pneumoniae (ATCC 31488) | 11 | 15 |
| Kl. pneumoniae (DL raw water) | 6 | 5.7 |
| Kl. oxytoca (ATCC 49131) | 4 | 4 |
| Serr. marcescens (Q/C 3) | 15 | 18 |
| Serr. marcescens (Waterloo) | 9 | 7 |
| Average Detection | 9.3 | 9.7 |
| Aero. hydrophila (MG1) | 0 | 0 |
| Ps. aeruginosa (ATCC 9027) | 0 | 0 |
| Neg. Control | 0 | 0 |

Example 2

Enzyme substrates can be used differentiate target bacteria. The end-products of enzyme substrates can generate optical signals at different wavelengths that can be separately detected using optical filters. Fluorescein di-β-D-galactopyranoside (FDG) and 4-methylumbelliferyl-β-D-glucuronide (MUG) were chosen to detect coliforms and E. coli. Bacteria were grown as above on 0.45 μm membranes in SG-II media comprising the chosen enzyme substrates and the end products of these substrates were detected using the imaging system described above with Ultraviolet light (UV). When excited at 365 nm (UV), FDG has an emission peak at 525 nm, while MUG has an emission peak at 450 nm. Coliforms hydrolyze FDG substrate while E. coli hydrolyze both FDG and MUG. See Table 2. Thus, a long-pass filter ($\lambda_c$=430 nm) was used to detect the presence or absence of emission signals. Where signal was detected, a 450 nm band-pass filter was used to determine if E. coli was present. If E. coli was not present, coliforms were present. The presence of E. coli and coliforms could be detected.

TABLE 2

| | Coliform | E. coli |
|---|---|---|
| FDG | Positive | Positive |
| MUG | Negative | Positive |
| Optical detection | 500 nm long-pass (+) | 500 nm long pass (+) |
| | 450 nm long-pass (−) | 450 nm long-pass (+) |

The quantitative detection of coliforms and E. coli can be achieved by combining the presence/absence information from each site using MPN methods.

Example 3

An about 5 hour SG/MF (a membrane filtration membrane combined with SG medium) was compared to a 24 hour COLILERT®/Qtray device. Portland, Me. primary effluent waste water was used as a test sample. A standard injured organism protocol (U.S. EPA Alternative Testing Protocol for chlorinating samples for injured organism studies) was used to achieve an at least 2 log reduction of target organisms. The procedures above were used to detect bacteria. The results are shown in Table 3.

TABLE 3

| Source | MF on SG for about 5 hours | Colilert ® in Qtray for 24 hours |
|---|---|---|
| Portland waste water with 2-log reduction | 9 CFU | 9.8 CFU |
| Negative control | 0 | 0 |

What is claimed is:

1. A detection device comprising:
    a) a container having an upper compartment and a lower compartment, wherein the upper compartment is connected to a passage through which a fluid sample can flow and enter the upper compartment, and wherein the lower compartment is connected to a passage through which a fluid sample can flow and exit the lower compartment;
    b) a mounting structure upon which a filter can be positioned,
    c) a filter, wherein the filter separates the upper compartment from the lower compartment, wherein the filter comprises a chromogen;
    d) a first template covering the filter, wherein the first template comprises a predetermined number of holes through which a liquid sample can flow through to discrete locations on the filter; and
    e) an absorbent pad under the filter and in contact with the filter.

2. The detection device of claim 1, wherein the upper compartment is separable from the lower compartment.

3. The detection device of claim 2, wherein the upper compartment and lower compartment are separable by twisting the upper compartment relative to the lower compartment.

4. The detection device of claim 1, wherein the discrete locations on the filter have an area of about 100 square millimeters or less.

5. The detection device of claim 1, wherein the template comprises at least about 10, 20, 50, or 100 holes.

6. The detection device of claim 1, wherein the template is sealed onto the filter.

7. The detection device of claim 1, wherein the template is plastic.

8. The detection device of claim 7, wherein the plastic template is compressed against the filter.

9. The detection device of claim 1, wherein the chromogen is an enzyme substrate that can be hydrolyzed by enzymes produced by a microorganism or cell.

10. The detection device of claim 9, wherein the filter comprises one or more different enzyme substrates at one or more different discrete locations.

11. The detection device of claim 1, further comprising a second template wherein the second template is in contact with the surface of the absorbent pad that is opposite of the surface of the absorbent pad that is in contact with the filter, wherein the second template comprises a predetermined number of holes through which a liquid sample can flow through to the lower compartment.

12. The detection device of claim 1, where in the absorbent pad comprises a growth medium or a combination thereof.

* * * * *